(12) United States Patent
Guler et al.

(10) Patent No.: US 6,300,309 B1
(45) Date of Patent: Oct. 9, 2001

(54) METHOD AND COMPOSITION FOR THE TREATMENT OF OSTEOPOROSIS

(75) Inventors: Hans-Peter Guler, Emeryville, CA (US); Satish Bhatia, Summit, NJ (US)

(73) Assignee: Novartis Corporation, New York, NY (US)

( * ) Notice: Subject to any disclaimer, the term of this patent is extended or adjusted under 35 U.S.C. 154(b) by 0 days.

(21) Appl. No.: 08/243,520

(22) Filed: Jun. 1, 1994

Related U.S. Application Data

(63) Continuation of application No. 07/850,545, filed on Mar. 13, 1992, now abandoned.

(51) Int. Cl.$^7$ .......................... A61K 38/16; A61K 38/00
(52) U.S. Cl. ................................. 514/12; 514/8
(58) Field of Search ........................... 514/8, 12

(56) References Cited

U.S. PATENT DOCUMENTS

| | | | |
|---|---|---|---|
| 4,642,120 | * 2/1987 | Nevo et al. | 623/16 |
| 4,861,757 | * 8/1989 | Antoniades et al. | 514/21 |
| 5,118,667 | * 6/1992 | Adams et al. | 514/12 |
| 5,210,074 | * 5/1993 | Nakamski et al. | 514/12 |

FOREIGN PATENT DOCUMENTS

| | | |
|---|---|---|
| 123228 | 10/1984 | (EP) . |
| 0 289 314 A2 | 11/1988 | (EP) . |
| 318184 | 5/1989 | (EP) . |
| 434625 | 6/1991 | (EP) . |
| 436469 | 7/1991 | (EP) . |
| 0440989 | 8/1991 | (EP) . |

OTHER PUBLICATIONS

CA: 115(14) #142160u–Stephan et al. Oct. 1991.*
CA: 115(22) #239741X–Buerk Dec. 1991.*
Humbel, Rene E., (1990) "Insulin–Like Growth Factors I and II" *Eur. J. Biochem.* 190:445–462.
Merimee, Thomas J., (1987) "Insulin–Like Growth Factors in Pygmies" *The New England Journal of Medicine* 316(15):906–911.
Conover et al, Insulin–Like Growth Factor I/Somatomedin–C and Glucocorticoids Synergistically; J. Cellular Physiology 116: 191–197(1983).
Schoenle et al, Insulin–Like Growth Factor I Stimulates Growth in Hypophysectomized Rats, Nature vol.296, No. 5484, 252–253(1982).
Stracke et al, Effect of Growth Hormone on Osteoblasts And Demonstration of Somatomedin–C/IGFI in Bone Organ Culture, Acta Endocrinologia 1984, 107:16–24.
Gotfredson et al, Total Body Bone Mineral in Vivo by Dual Photon Absorptiometry, Clinical Physiology (1984) 4, 343–355.
Schwander et al, Synthesis And Secretion of Insulin–Like Growth Factor . . . , Endocrinology vol. 113, No. 1, 297–305 (1983).

Bennett et al, Characterization of Insulin–Like Growth Factor I . . . , Endocrinology vol. 115, No. 4, 1577–1583 (1984).
Abstract #549, p. S 221 of Mueller et al, Insulin–Like Growth Factor–I increases Trabecular Bonemass in the Ovariectomized Rats, Aug. 26, 1991.
Abstract #548, p. S221 of Kalu et al, Insulin–Like Growth Factor–I Partially Prevents Ovarietomy Enduced Bone Loss, Aug. 26, 1991.
Stedmans Medical Dictionary 24$^{th}$ Ed. 1982, p. 1301, 1302.
Ott, Annals of Internal Medicine, vol. 104, No. 6, Jun. 1986, 874–876.
Canalis et al, Metabolism, vol. 26, No. 10, (Oct. 1977) 1079–1087.
Canalis, J. Clin. Invest., vol. 66, Oct. 1980, 709–719.
Isgaard et al, Am. J. Physiol. 250 (Endocrinol. Metab. 13): E. 367–E 372, 1986.
Bennett et al, J. Clinical Endocrinology & Metabolism, vol. 59, No. 4, 701–704 (1984).
Raisz, New England Journal of Medicine, vol. 318, No. 13, p. 818–828 (1988).
Buul–Offers. et al, Pediatric Research vol. 20, No. 9, 825–827, 1986.
Russel et al, Endocrinology 116:2563–2567 (1985).
Seyodin et al, J. Bioldgical Chemistry vol. 261, No. 13, 5693–5695 (1985).
Tashjian et al, Proc. Natl. Acad. Sci. USA, vol. 82, 4535–4538 (Jul. 1985).
Guler et al, Proc. Natl. Acad. Sci. USA, vol. 85, 4889–4893 (Jul. 1988).
Chiron Corp. Annual Report 1987 (1 page).
Simpson, Physiol. 235, E613–E616, Dec. 1984, Growth Factors Which Affect Bone.
Sara et al, Proc. Natl. Acad. Sci. USA, vol. 83, 4904–4907, (Jul. 1986).
Ballard et al, Biochemical And Biophysical Res. Commun. vol. 149, No. 2, 398–404, 1988.
Tseng et al, Biochemical And Biophysical Res. Commun. vol. 149, No. 2, 672–679, 1988.
Cascieri et al, Endocrinology, vol. 123, No. 1, 373–381 (1988).
Bayne et al, J. Biolocical Chemistry, vol. 263, No. 13, 6233–6239 (1988).
Sara et al, Biochemical And Biophysical Res. Commun. vol. 165, No. 2, 766–771 (1989).
QDR–1000 Product Literature (6 pages) (1989).
Kimmel, Radiologic Methods . . . , Annals Internal Medicine 1984, 100:908–911.

(List continued on next page.)

Primary Examiner—Theodore J. Criares
(74) Attorney, Agent, or Firm—Gregory D. Ferraro

(57) ABSTRACT

A method for the treatment or prevention of osteoporosis in higher mammals is disclosed, the method comprising administering Insulin-like Growth Factor I (IGF-I) in an effective amount thereof to said mammal, said mammal being in need of said treatment or prevention. Compositions for pharmaceutical use in the above method are also described.

12 Claims, 6 Drawing Sheets

OTHER PUBLICATIONS

Riggs, American J. of Medicine, vol. 91(Suppl. 5B) 37S–41S (Nov. 1991).

Lindsay, American J. of Medicine, vol. 91 (Suppl. 5B) 10S–13S (Nov. 1991).

Heaney, American J. of Medicine, vol. 91 (Suppl 5B) 23S–28S (Nov. 1991).

Chem Abstract 108:50024e, 1988 of Hoek et al, Endocrinology 122(1), 254–260 (1988).

* cited by examiner

METHOD AND COMPOSITION FOR THE TREATMENT OF OSTEOPOROSIS

This application is a continuation of application Ser. No. 07/850,545, filed Mar. 13, 1992 now abandoned.

FIELD OF THE INVENTION

The present invention concerns a method for the treatment of higher mammals having or being at substantial risk of developing osteoporosis in cortical bone, the treatment comprising the administration of insulin-like growth factor I (IGF-I). Hence, the invention is directed to the fields of bone growth and degeneration, to IGF-I, and to compositions thereof for use as pharmaceuticals.

BACKGROUND OF THE INVENTION

Osteoporosis encompasses a broad range of clinical syndromes having varying etiologies. In postmenopausal women, for example, two distinct types of osteoporsis have been identified. Type I osteoporosis occurs mainly in the early postmenopausal period from about age 50–65. It is characterized by excessive resorption, primarily in trabecular bone. Vertebral fractures are common. If given prior to significant bone loss, treatment which decreases or prevents bone resorption (such as with estrogen or calcitonin) is considered effective therapy.

Type II osteoporosis (a.k.a. senile osteoporosis) occurs essentially in all aging women and, to a lesser extent, in men. It is characterized by proportionate loss of cortical bone as well as trabecular bone. Here decreased bone formation plays a major role, if not a more important role than increased bone resorption. Fractures of the hip are characteristic of this type of osteoporosis.

Currently approved therapeutic agents for osteoporosis are antiresorptives. As such, while they may prevent further loss in patients with Type I osteoporosis, they are not as effective in reversing osteoporosis of either Type I or Type II or in halting Type II osteoporsis. See The American Journal of Medicine, Vol. 91 (Suppl 5B) 37S–41S; The American Journal of Medicine, Vol. 91 (Suppl 5B) 10S–13S; and The American Journal of Medicine, Vol. 91 (Suppl 5B) 23S–28S. In addition, the most widely accepted preventive agent for osteoporosis currently in use is estrogen therapy, which is not really an acceptable therapeutic agent for women with a history of or at risk for breast or endometrial cancers (estrogen dependent tumors) or for men with osteoporosis.

Insulin-like Growth Factor I (IGF-I) is a 70 amino acid peptide belonging to a family of compounds under the class name somatomedins and retains some structural and biologically similarities to insulin. The somatemedins' activity lie on a spectrum from hypoglycemic effects similar to insulin to growth promoting effects which are exemplified by growth hormone. IGF-I predominately induces growth and cell proliferation. IGF-I has also been demonstrated to specifically bind to receptors on rat osteoblast-like bone cells (Bennett et al, Endocrin. 115(4):1577–1583, 1984). IGF-I is routinely fabricated in the liver and released for binding to carrier proteins in the plasma (Schwander et al, Endocrin. 113(1):297–305, 1983), which bound form is inactive. In addition, there is a biofeedback regulating loop involving the somatomedins and growth hormone such that higher somatomedin concentrations inhibit growth hormone release which results in lesser production of endogenous IGF-I.

IGF-I infused into rats has been shown to result in markedly greater increases in body weight gain compared to controls, with increases in tibial epiphyseal width and thymidine incorporation into costal cartilage (Nature 107: 16–24, 1984) and directly stimulate osteoblasts to result in a greater number of functional osteoblasts. IGF-I is also mentioned as the vehicle through which growth hormone's effects on bone is mediated in Simpson, Growth Factors Which Affect Bone, Physiol. 235, TIBS, December 12, 1984.

Nevertheless, it is important to note that the foregoing pre-clinical studies were conducted with fetal or newborn rat cells. It is highly likely that such "young" cells are more responsive to IGF-I (as well as other influences) than older cells, especially those in the elderly with established osteoporosis or those with drug induced or environmentally induced defects leading to reduced bone density. Furthermore, in J. Bone and Mineral Res., Vol 6, Suppl 1, Abstr. 549, p. S-221, August 1991, the authors report that IGF-I has virtually no effect on cortical bone of oovariectomized rats.

OBJECTS OF THE INVENTION

Accordingly, an object of the present invention is to provide a method of treatment of osteoporosis in higher mammals exhibiting decreased cortical bone mineral density and preventing osteoporosis due to cortical bone mineral density reduction in such mammals clinically prone to such cortical bone density reductions.

Another object of the invention is to provide pharmaceutical compositions useful in achieving the foregoing object.

SUMMARY OF THE INVENTION

Surprisingly, these and other objects of the invention have been achieved with the finding that IGF-I is useful in the treatment of osteoporosis in higher mammals exhibiting decreased cortical bone mineral density and those exposed to drugs or environmental conditions which tend to result in cortical bone mineral density reduction and potentially to a cortical bone osteoporotic condition.

DETAILED DESCRIPTION OF THE INVENTION

The present invention concerns osteoporosis treatment and prevention, which osteoporosis is associated with decreased cortical bone mineral density in mammals generally, but is especially suited for the treatment and prevention of such osteoporosis in humans.

For the present invention purposes, mammals includes all mammals within the taxonomic orders of Primates, Carnivora, Perissodactyla and Artiodactyla. This includes, without limitation, Old World monkeys, New World monkeys, great apes, humans, cats, dogs, horses, pigs, cattle, sheep, and goats. Preferably mammals are selected from the taxonmic orders of Primates, Carnivora, Perissodactyla, and Artiodactyla, more preferably Primates, cats, dogs, sheep, goats, horses, pigs and cattle, still more preferably Primates, most preferably humans.

IGF-I is a naturally occuring protein that can be obtained from a number of sources. Preferably, IGF-I from the same species (or its synthetic twin) as the species being treated therewith is employed, but IGF-I from one species may be used to treat another species if the immune response elicited is slight or non-existent. In addition, fragments and analogs of IGF-I having IGF-I activity, particularly IGF-I anti-osteoporosis activity, are also suitably employed in the invention. As used within the context of the present invention IGF-I includes such fragments and analogs unless the text clearly states otherwise. Where weights of IGF-I are presented, that weight of IGF-I or an approximately equipotent weight of such analogs and fragments are intended absent clear direction to the contrary. Where no type of IGF-I is indicated, reference is to human-IGF-I (meaning the structure, not the species source), unless the reasonable reading of the text requires otherwise.

IGF-I analogs and fragments of IGF-I or its analogs are commonly known in the art as can be seen from Proc. Natl. Acad. Sci. USA, Vol 83, pp. 4904–4907, July 1986; Biochemical and Biophysical Research Communications, Vol 149, No. 2, pp. 398–404, Dec. 16, 1987; Biochemical and Biophysical Research Communications, Vol. 149, No. 2, pp. 672–679, Dec. 16, 1987; Endocrinology, Vol. 123, No. 1, pp. 373–381; The Journal of Biological Chemistry, Vol. 263, No. 13, pp. 6233–6239, May 5, 1988; and Biochemical and Biophysical Research Communications, Vol. 165, No. 2, pp. 766–771, Dec. 15, 1989.

IGF-I can be synthetically produced, chemically or by recombinant techniques, as well as extracted from tissues. Recombinant manufacture is preferred. One such recombinant technique is disclosed in EP 123,228, incorporated herein by reference.

An effective amount of IGF-I for the present invention is an amount sufficient to slow, stop, or reverse the cortical bone mineral density reduction rate in a patient exhibiting cortical bone mineral density reduction. Throughout the specification where values are given for non-cortical bone tissue they are for purposes of exemplifying the osteoporotic state generally. In the normal healthy 20–25 year old human population, bone mineral density in the spine (using dual photon densitometry) typically is in the range of 0.85 to 1.9 $g/cm^3$, usually 0.9 to 1.85 $g/cm^3$, and most 1.0 to 1.8 $g/cm^3$; and in the mid radius and distal radius it is typically 0.7–1.4 $g/cm^3$, usually 0.75–1.3 $g/cm^3$, and most often 0.8–1.2 $g/cm^3$. Exemplary non-limiting normal ranges are shown in the Figures along with osteoporosis distributions. Norms using other techniques will be apparent from the literature and general experience therewith as experience with such techniques grow. Of course, it is to be remembered that different sub-populations have different norms in bone mineral density. For example, caucasian women typically differ in this parameter from caucasion men as well as from black women, oriental women, and women of other racial types. It is also important to remember that the present invention is directed to treating those with bone mineral which is (a) totally below either the normal bone mineral density range for the population generally or for the patient sub-population or (b) below 1.0 $g/cm^3$ or (c) below the fracture threshold (approximately 2 standard deviations below the mean bone mass for the population at age 35). The fracture threshold for the spine, for example, is defined as the bone mineral density value below which 90% of all patients with one or more compression fractures of the spine are found. (See Mayo Clin. Proc., December 1985, Vol 60, p. 829–830). In addition, anyone who demonstrated a statistically significant reduction in bone density over a previous measurement, regardless of where that patient is in the typical ranges above, is a patient to whom the present invention treatment is directed. Statistical significance in this context will vary with the technique employed to measure bone mineral density, as well as with the sensitivity of the instruments used. However, with instrumentation and techniques generally available in 1988, a 1 or 2% change in bone mineral density from the earliest measurement to the most recent is not considered statistically significant. Still as techniques and equipment improve, persons of ordinary skill in the field of bone mineral density measurement will revise downward the maximum percent change which is not considered statistically significant.

Current bone mineral density measurement techniques include dual energy radiography, quantitative computerized tomography, single photon densitometry, and dual photon densitometry. These techniques will be well known to those of ordinary skill in the art; however, descriptions thereof can be found in: Mayo Clin. Proc., December 1985, Vol. 60, p. 827–835; Orthopedic Clinics of North America, Vol. 16, No. 3, July 1985, p. 557–568; Hologic QDR™-1000 Product Literature; Annals of Internal Medicine, 1984, 100:908–911; and Clinical Physiol 4:343, 1984.

Notwithstanding the lack of statistical significance of a particular result, any bone mineral density reduction should be followed for further reductions, which cumulatively may be significant.

Usually, an effective amount of IGF-I, when given parentally (intravenously, subcutaneously, intramuscularly, etc.) is between 2.5 $\mu g/Kg/day$ up to about 180 $\mu g/Kg/day$, preferably about 5$\mu g/Kg/day$ up to about 150 $\mu g/Kg/day$, more preferably 10 $\mu g/Kg/day$ up to about 120 $\mu g/Kg/day$, even more preferably 10 $\mu g/Kg/day$ up to about 100 $\mu g/Kg/day$, still more preferably about 10 $\mu g/Kg/day$ up to about 90 $\mu g/Kg/day$. When given continuously, such effective amount may be given in two or three doses spread over time such as by IV drip or subcutaneous injection(s) with the total daily dose being spread across a portion or the entire administration period. Typical continuous dosing is in the range of 2.5 $\mu g/Kg/hour$ lto about 50 $\mu g/Kg/hour$, preferably about 5 $\mu g/Kg/hour$ up to about 25 $\mu g/Kg/hour$, although wider ranges of "continuous" administration amounts will be apparent to those of ordinary skill in the art. When given by subcutaneous injection, it is most preferably administered from 2 times/wk up to 3 times a day, preferably 3 times a week up to once or twice daily. Particularly suitable doses are 10, 15, 30, and 60 $\mu g/Kg/day$.

The specific dosage for a particular patient, of course, has to be adjusted to the degree of response, route of administration, the individual weight and general condition of the patient to be treated, and is finally dependent upon the judgment of the treating physician.

In general, the pharmaceutical preparations for use in the present invention comprise an effective amount of IGF-I or an active fragment or analog or fragment of an analog thereof together with a pharmaceutically and parentally acceptable carrier or adjuvant. Compositions having an approximately 6 day supply typically contain from about 0.1 mg to 15 mg, preferably 1 mg to 13 mg, more preferably about 3 mg to about 10 mg, most preferably 5 mg to 10 mg of IGF-I. The liquid carriers are typically sterile water, approximately physiologic saline, about 0.1 M acetic acid, approximately 5% aqueous dextrose, etc; preferably sterile water, physiologic saline, or 5% aqueous dextrose.

The carriers and adjuvants may be solid or liquid and may be organic or inorganic. The active compound and the compositions of the invention are preferably used in the form of preparations or infusions for parenteral (subcutaneous, intramuscular, or intravenous) administration. Such solutions are preferably isotonic aqueous solutions or suspensions which can be prepared before use, for example by reconstituting a lyophilized preparation of the active agent. The pharmaceutical preparations may be sterilized and/or contain adjuvants, for example preservatives, antiinfectives, stabilizers wetting agents, emulsifiers, solubilizers, tonicity regulating agents, and/or buffers. Other adjuvants will of course be apparent to those of ordinary skill in the art. Other dosage forms and routes of administration for use in the present invention include aerosols and sprays for lung inhalation or as a nasal spray, transdermal patch administration, and buccal administration.

The present pharmaceutical preparations, which, if desired, may contain further pharmacologically active or otherwise pharmaceutically valuable substances, especially bone antiresorptives such as estrogen, calcitonin, and bisphosphonates, particularly 3-aminopropyl-1hydroxy-1, 1-bisphosphonate, are prepared from their constituent parts by techniques known in the art, for example lyophilization, dissolution, reconstitution, and suspension techniques, among others known to those of ordinary skill. They typically contain from about 0.1% to about 100% of active ingredient, but especially in the case of a solution from about 1% to about 20% and especially in the case of a lyophilizate up to 100% of active ingredient.

DESCRIPTION OF THE DRAWINGS

FIGS. 1 and 2 are taken from Mayo Clin. Proc., Vol. 60, December 1985, mentioned above, and are based on data from Riggs B L, Wahner H W, Dunn W L, Mazess R B, Offord K P, Melton L J III: Differential changes in bone mineral density of the appendicular and axial skeleton with aging: relationship to spinal osteoporosis, J. Clin. Invest. 67:328–335, 1981.

FIGS. 3–6 are taken from Orthopedic Clinics of North America, Vol 16 No 3, July 1985, mentioned above.

Figures 1A, 1B, 1C:
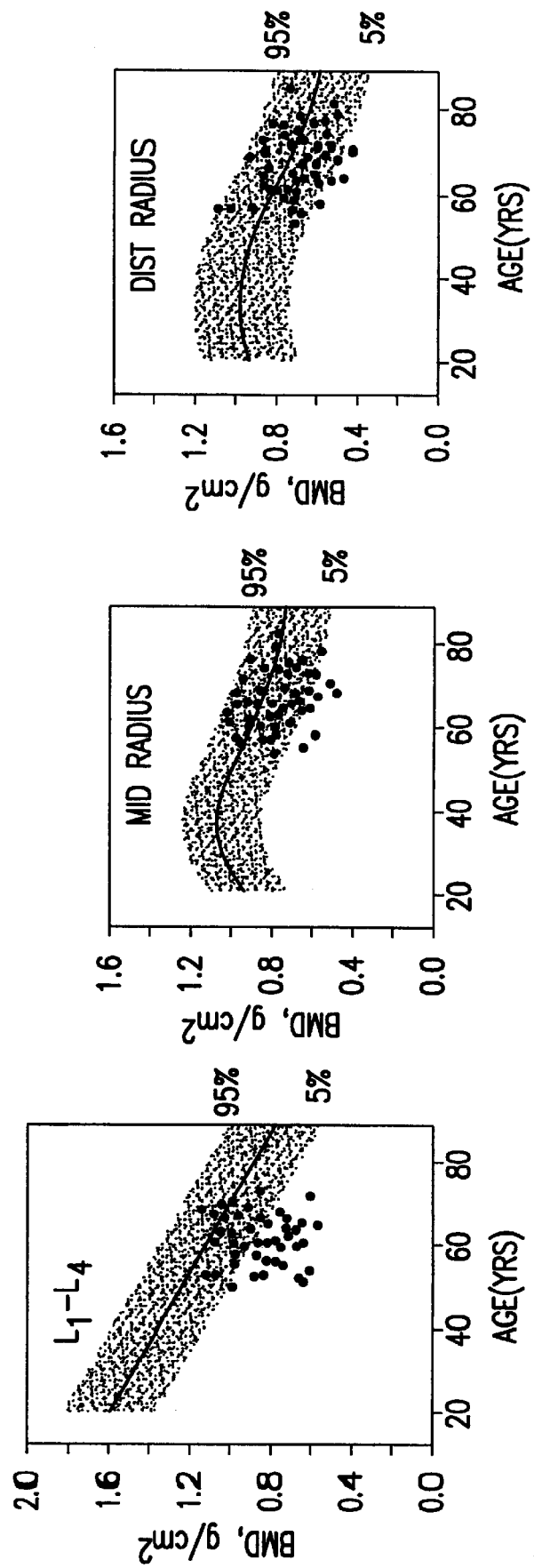
FIG. 1. Bone mineral density (BMD in spine (1A); (L1–4; measured with use of dual-photon absorptiometry)), midradius (1B), and distal radius (1C) (measured with use of single-photon absorptiometry) in 76 women with osteoporosis in comparison with age- and sex-adjusted normal range (105 women). Shaded areas represent 5th and 95th percentile range of normals. Patients with osteoporosis are indicated by the dots. Note incomplete separation of the two populations. Spinal measurements result in the best distinction of patients with osteoporosis from normal subjects because this disease primarily affects trabecular bone of the spine.
Figure 2:
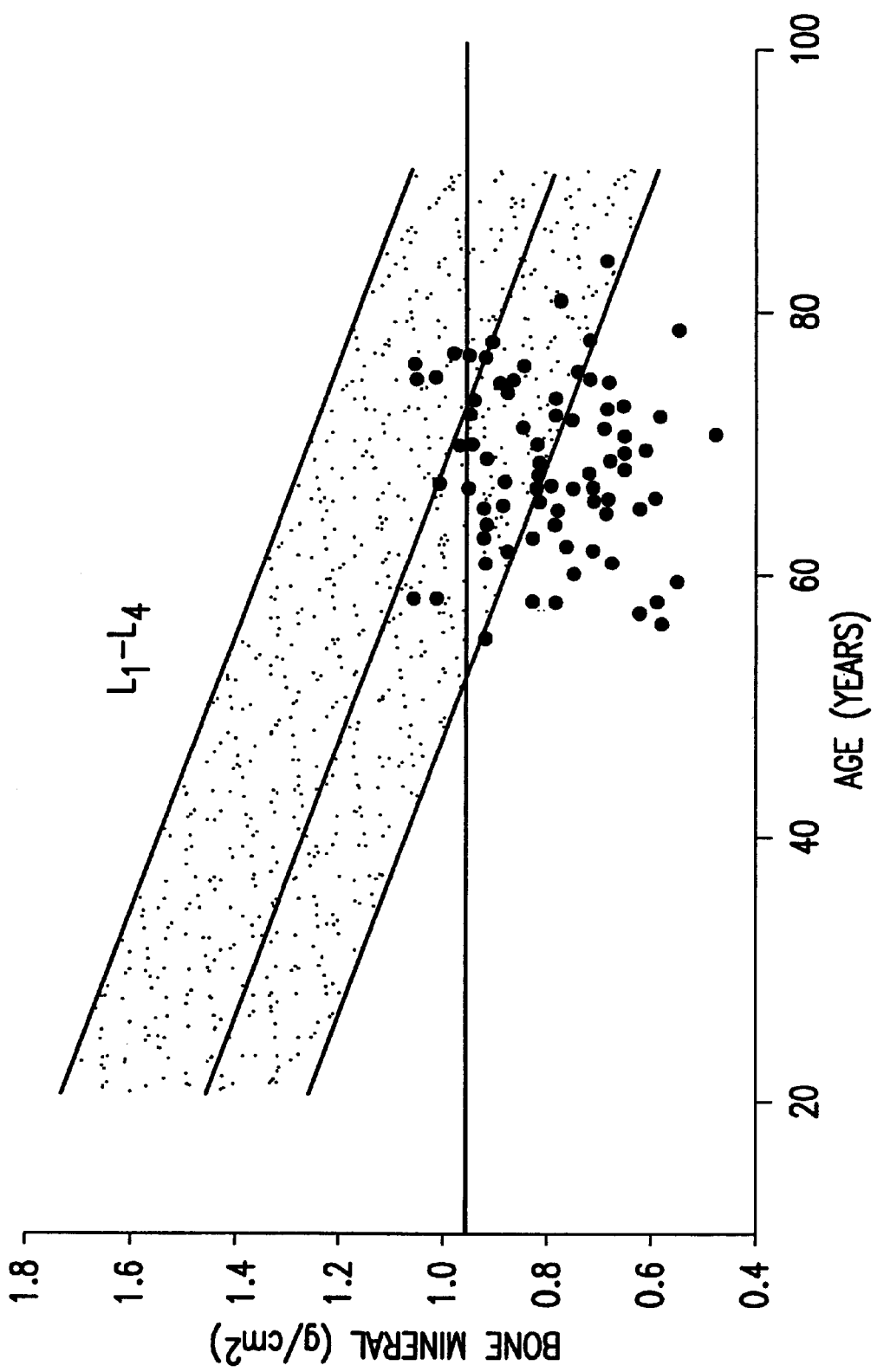
FIG. 2. Fracture threshold for spinal bone mineral (horizontal line) superimposed on normal range (shaded area) and values for 76 patients with osteoporosis (dots), as depicted in FIG. 1. With progressing age, values of increasing numbers of normal subjects are below the fracture threshold. Fracture threshold is approximately two standard deviations below mean bone mass at 35 years of age.
Figure 3A:
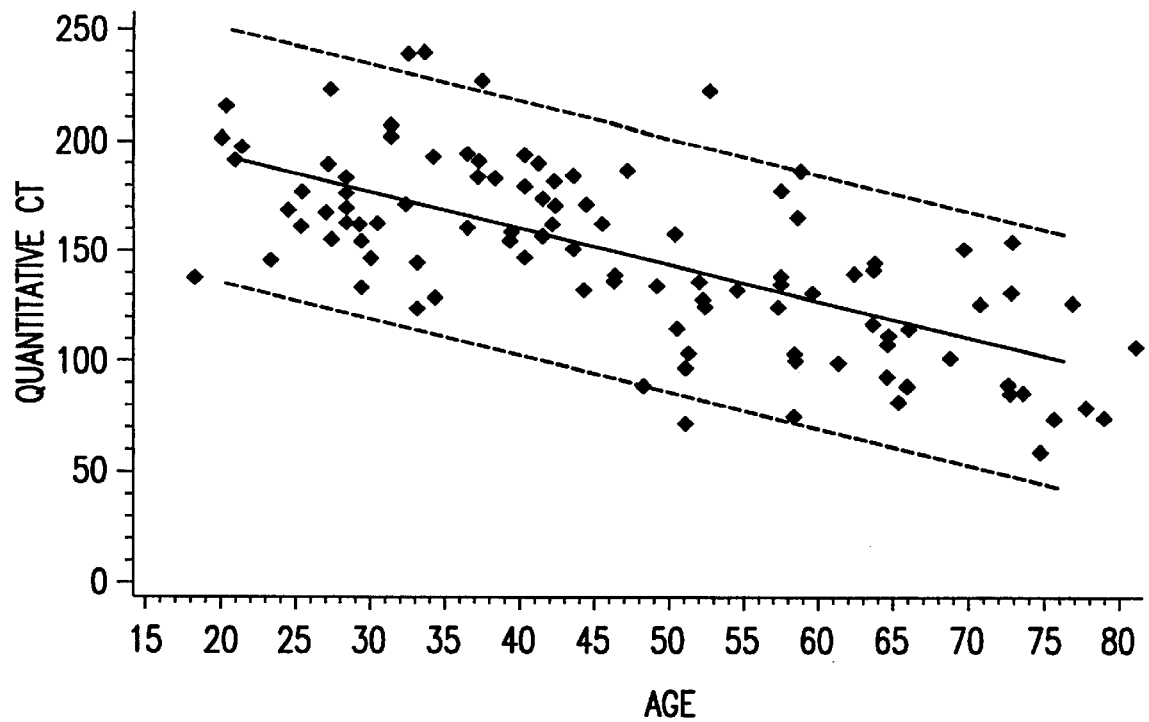
FIG. 3. A. Normal male values for vertebral cancellous mineral content by QCT, using cubic regression with 95% confidence intervals. The cubic regression gives only a slightly better fit to the data for men than does a linear regression (p<0.15). B. Normal female values for vertebral cancellous mineral content by QCT, using cubic regression with 95% confidence intervals (p<0.05). An accelerated loss is observed after menopause.
Figure 3B:
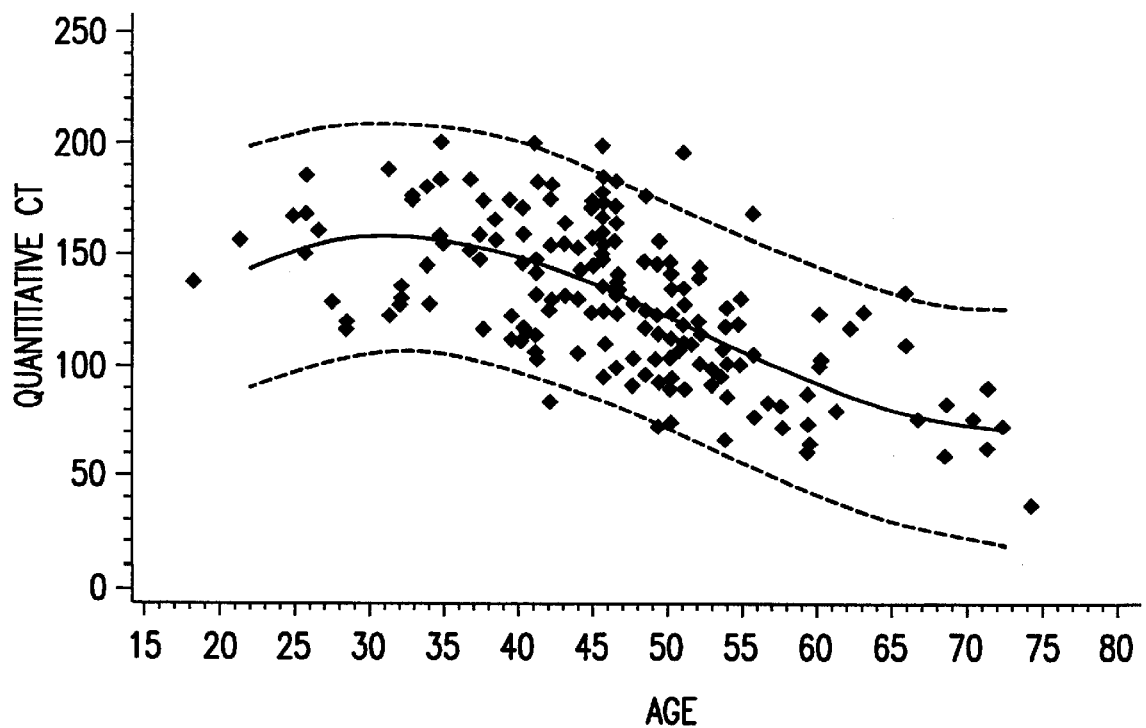
Figure 4A:
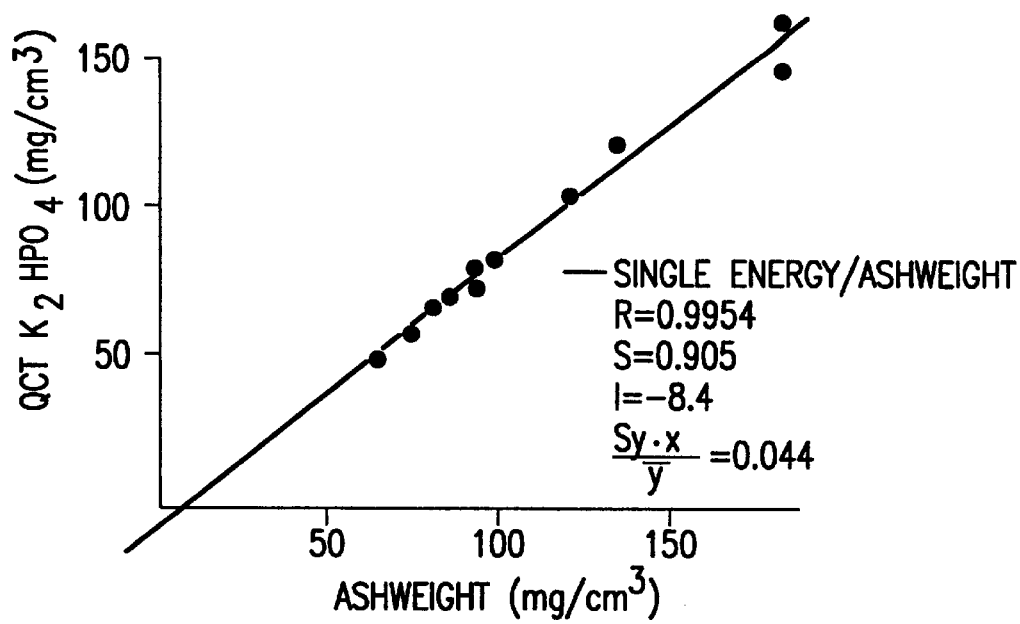
FIG. 4. A and B. The accuracy of single-energy QCT is shown for vertebral specimens (preserved in sodium azide) from 11 patients (10 men and 1 woman), ages 40–90 years.
Figure 4B:
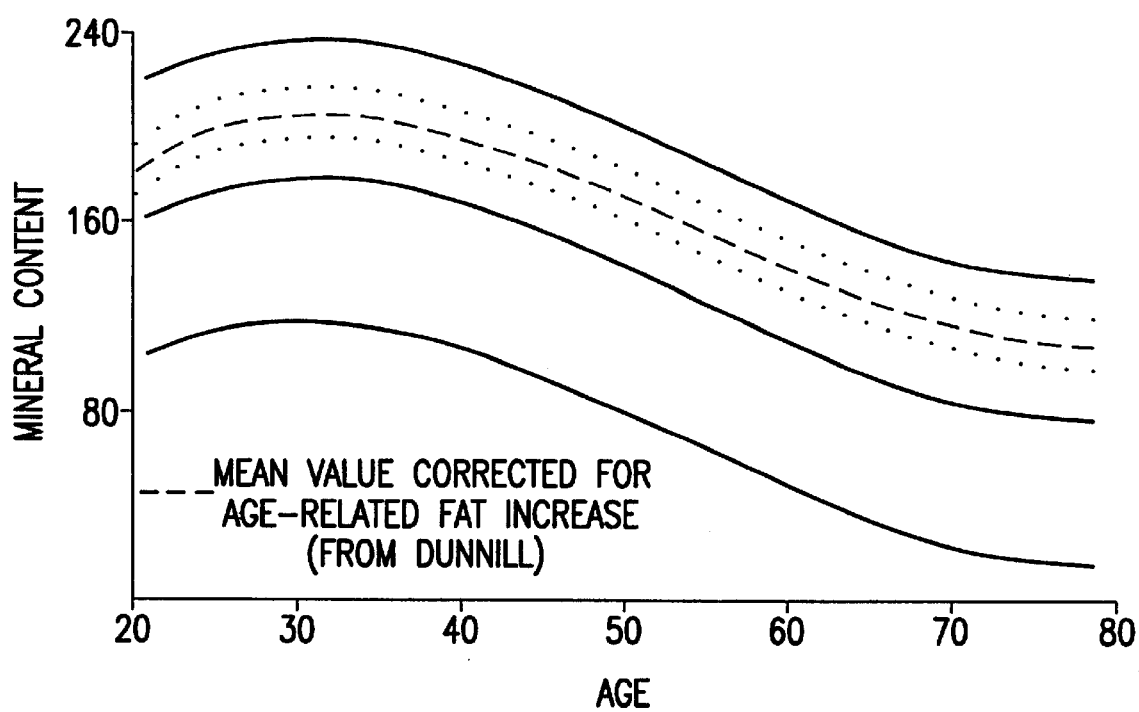
Figure 5:
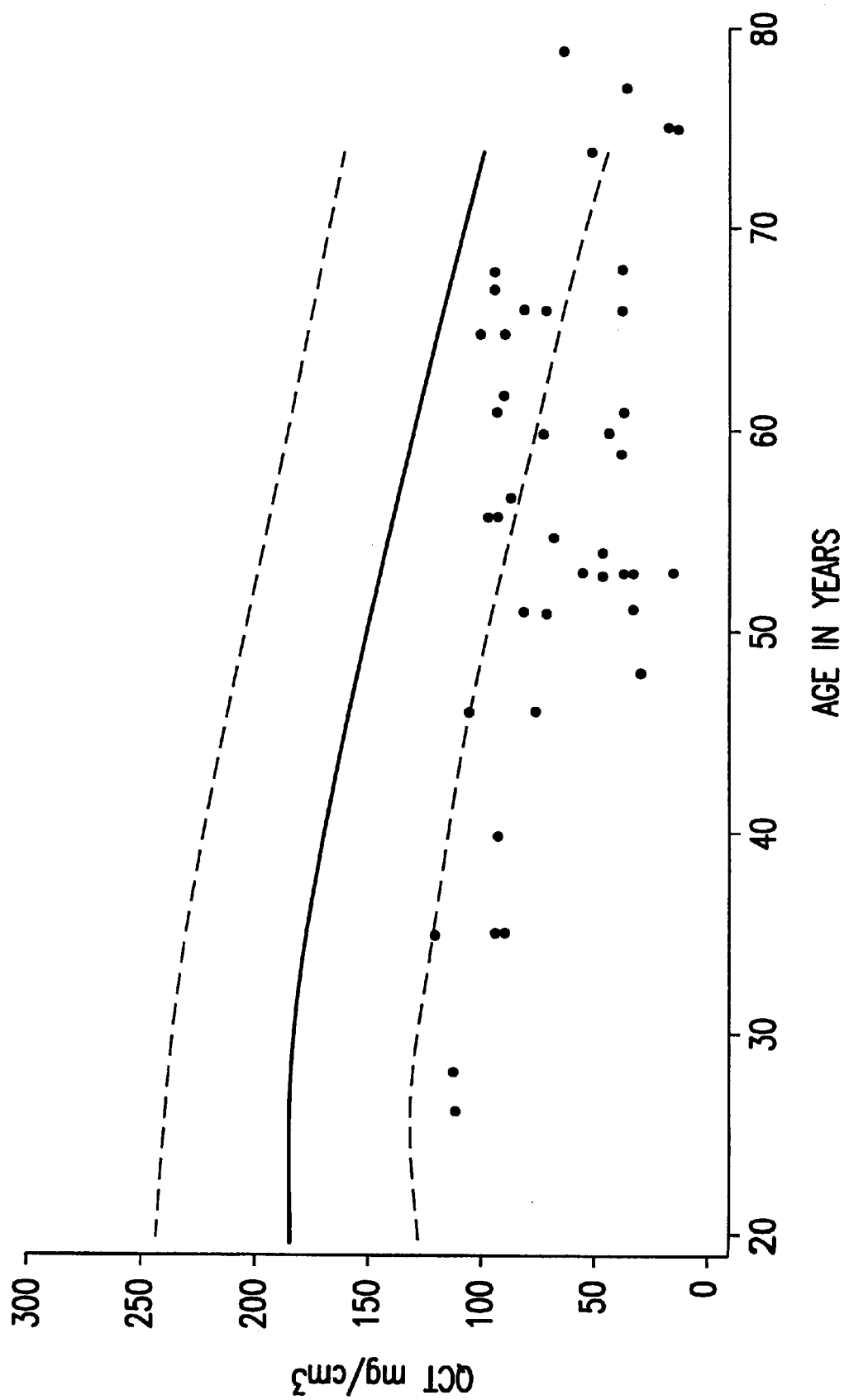
FIG. 5. Values for men with idiopathic osteoporosis and spinal fractures are plotted (black dots) against the normal male curve (cubic regression with 95% confidence intervals). A fracture threshold at approximately 11 mg/cm$^3$ is observed.
Figure 6:
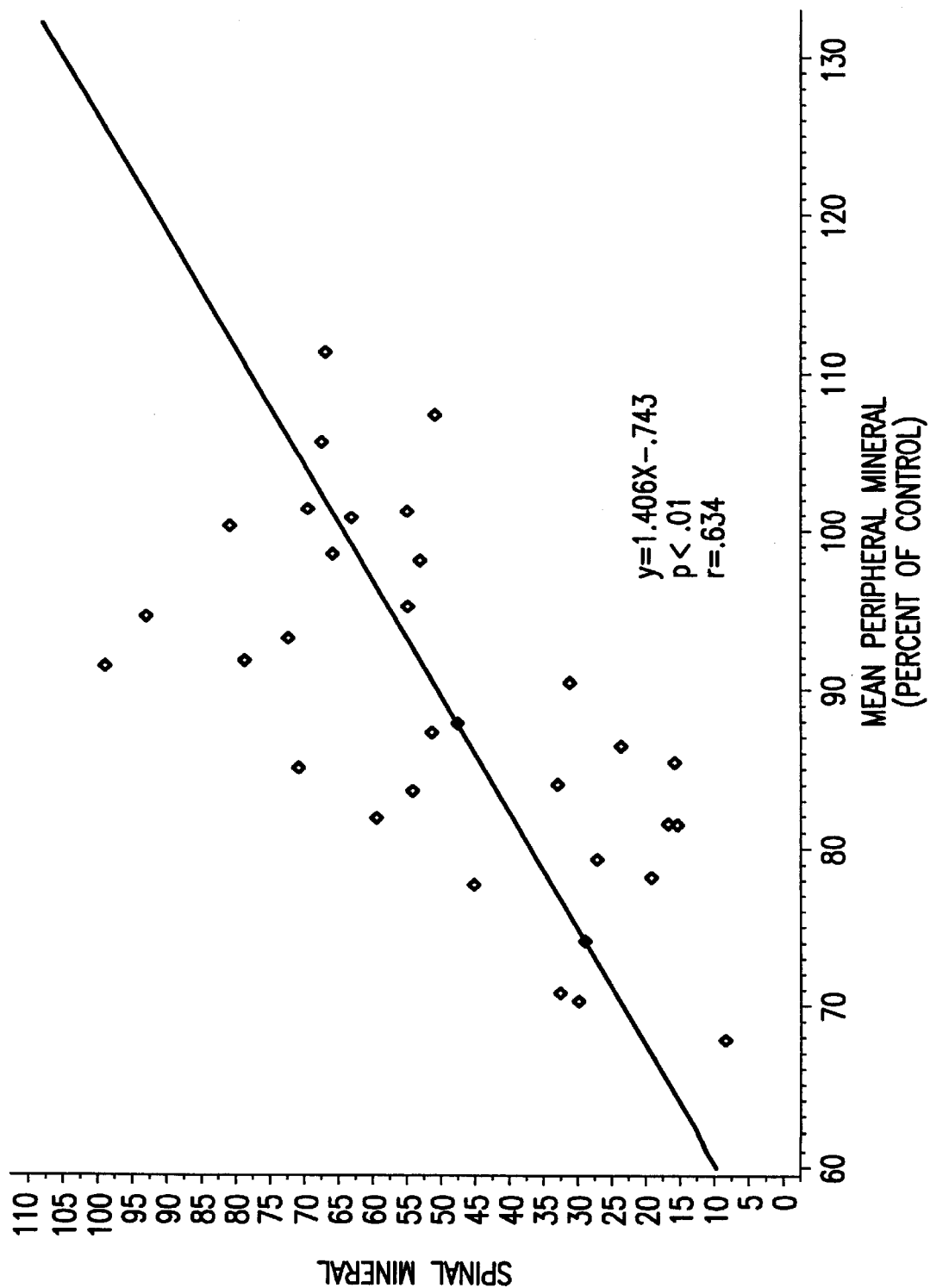
FIG. 6. Idiopathic osteoporotic male values showing larger decrement from normal for vertebral mineral QCT than for mean peripheral cortical mineral by radiogrammetry and photon absorptiometry.

Having fully described the instant invention, the following Examples are presented to more clearly set forth the invention without imposing any limits on the scope of the invention as set out in the claims.

EXAMPLES

Examples 1–3

Dry Ampules of IGF-I

Sterile, filtered 1% (w/v) aqueous solution of IGF-I is added, in the amount indicated to the respective dry ampules set forth below. The solution is then lyophilized to result in the dry ampules for reconstitution. The ampules are reconstituted with the indicated amount of sterile water, physiologic saline, 0.1 M acetic acid, or 5% aqueous dextrose to result in a reconstituted solution having the total volume as shown below. Each vial is sufficient for a 6 day course of treatment for the intended patient.

|  | Ex 1 | Ex 2 | Ex 3 |
|---|---|---|---|
| ampule size | 5 ml | 8 ml | 50 ml |
| IGF-I fill volume | 1 ml | 5 ml | 30 ml |
| reconstitution volume | 1 ml | 5 ml | 30 ml |

Example 4

6 beagles per group are used to demonstrate the ability of IGF-I to improve cortical bone density after loss of ovarian function. One group is given a sham operation to serve as a control. 4 other groups are oophorectomized. Of these 4, one group is treated with IGF-I immediately, one is given IGF-I after bone growth function has been reduced, one is treated with estrogen and one is followed without treatment. Each group is followed for a period of 12 months and bone mineral density (BMD) of the vertibral (trabecular) and femoral (cortical) bones are measured. The results, reported as average changes per group over the 8 month period are reported in Table I below.

TABLE I

| TREATMENT GROUP | % CHANGE IN BMD (12 MONTHS-0 TIME) CORTICAL BONE | % CHANGE IN BMD (12 MONTHS-0 TIME) TRABECULAR BONE |
|---|---|---|
| Sham Operation | 4.0% | 6.2% |
| Oophorectomized only | 0.4% | -1.4% |
| Oophorect. + imm. IGF-I | 10.1% | 12.3% |
| Oophorect. + estrog. |  |  |
| 4 months treatment after 8 months delay | 1.9% | 8.8% |
| Oophorect. + IGP-I |  |  |
| 4 months treatment after 8 months delay | 9.6% | 9.0% |

Not only did the treatment with IGF-I both prophylactically and therapeutically completely wipe out any loss in cortical bone growth associated with oophorectomy, it pushed cortical bone growth beyond the levels which were achieved by the sham operated controls by more than twice those values and beyond that acheived by estrogen by more than 4.5 times.

We claim:

1. A method for the treatment of osteoporosis in a mammal having reduced cortical bone mineral density or preventing the same in a mammal prone thereto comprising administering to said mammal an effective amount for said treatment or prevention of a compound selected from IGF-I, an active fragment thereof, an active analog thereof, or an active fragment of either IGF-I or its analog.

2. The method of claim 1 wherein said mammal is a human being.

3. The method of claim 1 wherein said IGF-I has the same amino acid sequence as natural IGF-I for the same species as the species to which said IGF-I is being administered.

4. The method of claim 1 wherein said compound is a naturally occurring.

5. The method of claim 1 wherein said compound is synthetically produced.

6. The method of claim 1 wherein said compound is produced by a recombinant technique.

7. The method of claim 1 wherein said compound is administered parenterally.

8. The method of claim 1 wherein said reduction in cortical bone mineral density in said mammal is in excess of 2% of any prior cortical bone mineral density measurement in said mammal.

9. The method of claim 1 wherein said reduction in cortical bone mineral density in said mammal is in excess of 4% of any prior cortical bone mineral density measurement in said mammal.

10. The method of claim 1 wherein said reduction in cortical bone mineral density in said mammal is in excess of 6% of any prior cortical bone mineral density measurement in said mammal.

11. The method of claim 1 wherein said reduced cortical bone mineral density is characterized as being at or below the lower 10th percentile of the general population of mammals of the same species between the ages of 1.5 times and twice reproductive maturity for said species.

12. The method of claim 11 wherein said mammal is a human being and said 1.5 times to twice reproductive maturity is the age bracket 20–25 years.

* * * * *